United States Patent
Goldstein et al.

(10) Patent No.: US 6,618,145 B1
(45) Date of Patent: Sep. 9, 2003

(54) SPECTROPLARIMETRIC REFLECTOMETER

(75) Inventors: Dennis H. Goldstein, Niceville, FL (US); David B. Chenault, Huntsville, AL (US); Monte Owens, Geneva, IL (US)

(73) Assignee: The United States of America as represented by the Secretary of the Air Force, Washington, DC (US)

( * ) Notice: Subject to any disclaimer, the term of this patent is extended or adjusted under 35 U.S.C. 154(b) by 0 days.

(21) Appl. No.: 09/679,199

(22) Filed: Oct. 5, 2000

Related U.S. Application Data
(60) Provisional application No. 60/176,766, filed on Jan. 19, 2000.

(51) Int. Cl.[7] .................................................. G01J 4/00
(52) U.S. Cl. ................................. 356/369; 356/364
(58) Field of Search .............................. 356/369, 364, 356/365, 366, 367; 250/225

(56) References Cited

U.S. PATENT DOCUMENTS

| | | | | |
|---|---|---|---|---|
| 4,077,720 A | * | 3/1978 | Kasai | 356/118 |
| 4,210,401 A | * | 7/1980 | Batten | 356/118 |
| 4,306,809 A | | 12/1981 | Azzam | 356/368 |
| 4,309,110 A | * | 1/1982 | Tumerman | 356/365 |
| 4,668,860 A | * | 5/1987 | Anthon | 250/225 |
| 4,681,450 A | | 7/1987 | Azzam | 356/367 |
| 4,917,461 A | | 4/1990 | Goldstein | 350/286 |
| 4,961,634 A | | 10/1990 | Chipman et al. | 350/403 |
| 5,045,701 A | | 9/1991 | Goldstein et al. | 250/339 |
| 5,247,176 A | | 9/1993 | Goldstein | 250/338.1 |
| 5,333,052 A | * | 7/1994 | Finarov | 356/369 |
| 5,973,787 A | * | 10/1999 | Aspnes et al. | 356/369 |
| 6,128,085 A | * | 10/2000 | Buermann et al. | 356/369 |
| 6,278,519 B1 | * | 8/2001 | Rosencwaig et al. | 356/369 |

OTHER PUBLICATIONS

"Photopolarimetric Measurement of the Mueller Matrix by Fourier Analysis of a Single Detected Signal," by R.M.A. Azzam, *Opt Lett*, 2(6), 148–150 (1978).
"Infrared Spectropolarimetry," by D.H. Goldstein et al, *Opt Eng*, 28(2), 120–125 (1989).
"Error Analysis of a Mueller Matrix Polarimeter," by D.H. Goldstein et al, *J Opt Soc Am*, 7(4), 693–700 (1990).
"Mueller Matrix Algorithms," by Chenault et al, *Proc SPIE* 1746, 231–246 (Jul. 1992).

* cited by examiner

*Primary Examiner*—Frank G. Font
*Assistant Examiner*—Layla Lauchman
(74) *Attorney, Agent, or Firm*—Bobby D. Scearce; Thomas L. Kundert

(57) ABSTRACT

A spectropolarimetric reflectometer for measuring polarimetric reflection properties of materials over broad spectral wavelength regions is described wherein radiation from a Fourier transform spectrometer passes through a set of polarization elements that serve as a polarization state generator and is reflected off the sample and collected by optics that includes a polarization state analyzer, focusing mirror and detector.

15 Claims, 1 Drawing Sheet

SPECTROPLARIMETRIC REFLECTOMETER

CROSS-REFERENCE TO RELATED APPLICATION

This application claims priority of the filing date of Provisional Application Serial No. 60/176,766 filed Jan. 19, 2000, the entire contents of which are incorporated by reference herein.

RIGHTS OF THE GOVERNMENT

The invention described herein may be manufactured and used by or for the Government of the United States for all governmental purposes without the payment of any royalty.

BACKGROUND OF THE INVENTION

The present invention relates generally to a spectropolarimetric reflectometer for measuring the polarization characteristics of materials in reflection over broad wavelength regions.

Many sensor systems rely on reflected light, from natural or manmade sources, to obtain the energy for their detector elements. The ability of the sensor system to detect and process reflected energy depends on knowledge of the reflection characteristics, including polarization properties, of the materials. An instrument is therefore needed that measures the polarization of reflected light over broad regions of the ultraviolet (UV), the visible and infrared (IR) spectrum in order to evaluate polarized reflection properties of materials.

Relevant prior art instrumentation includes an infrared spectropolarimeter for measuring polarization properties of materials in transmission, as described by Goldstein et al (U.S. Pat. No. 5,045,701 (Sep. 3, 1991)), the entire contents of which are incorporated by reference herein. The Goldstein et al '701 spectropolarimeter is based on a Fourier transform infrared spectrometer containing a dual rotating retarder Mueller matrix polarimeter in the sample compartment. Measurements can be made of polarization properties of transmissive samples over large wavelength regions into the infrared (2.5 $\mu$m and further into the IR).

The invention solves or substantially reduces in critical importance problems with prior art instruments by providing a polarimeter incorporating a modem Fourier transform spectrometer (FTS) that is capable of measurements over broad spectral regions from the UV to the far IR of samples in reflection, and is capable of rapid collection of more spectral and polarimetric information, primarily in the form of Mueller matrices, mathematical functions that completely describe the polarization properties of a sample, for each wavelength collected by the spectrometer, than any known instrument. The invention has substantial use in a broad range of applications, including electrooptic sensors, robotic vision, laser cutting and welding, and telecommunications.

It is therefore a principal object of the invention to provide a novel polarimeter.

It is another object of the invention to provide an instrument for measuring the polarization characteristics of materials in reflection over broad spectral wavelength regions.

It is a further object of the invention to provide a spectropolarimetric reflectometer operating over broad wavelength regions from the ultraviolet to the far infrared.

It is yet another object of the invention to provide an instrument for generating Mueller matrix functions describing the polarization properties of materials in reflection.

These and other objects of the invention will become apparent as the detailed description of representative embodiments proceeds.

SUMMARY OF THE INVENTION

In accordance with the foregoing principles and objects of the invention, a spectropolarimetric reflectometer for measuring polarimetric reflection properties of materials over broad spectral wavelength regions is described wherein radiation from a Fourier transform spectrometer passes through a set of polarization elements that serve as a polarization state generator and is reflected off the sample and collected by optics that includes a polarization state analyzer, focusing mirror and detector.

DESCRIPTION OF THE DRAWINGS

The invention will be more clearly understood from the following detailed description of representative embodiments thereof read in conjunction with the accompanying drawings wherein.

DETAILED DESCRIPTION

Figure 1:
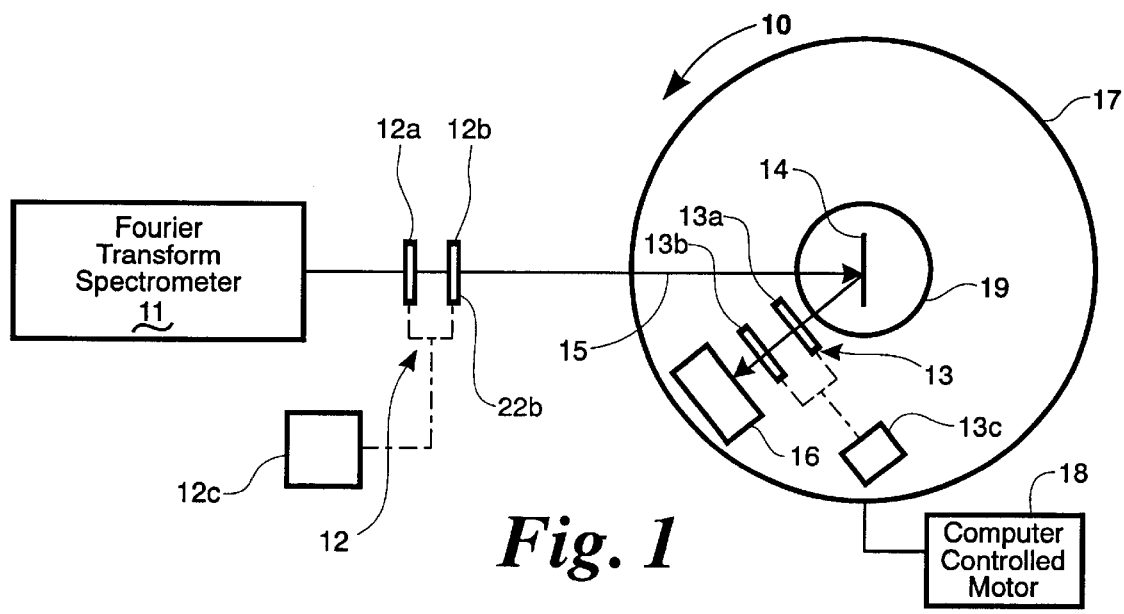
FIG. 1 is a schematic view of the system of the invention in the configuration for bistatic bidirectional reflectance distribution function (BRDF) measurements.
Figure 2:
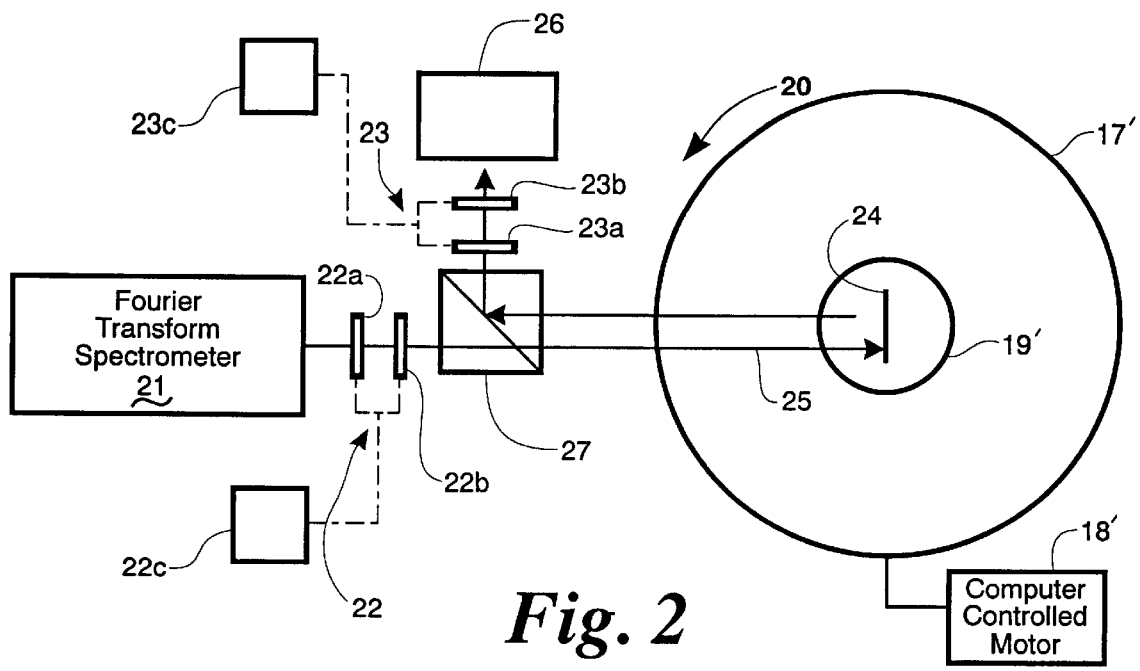
FIG. 2 is a schematic view of the system of the invention in the configuration for monostatic BRDF measurements.

Referring now to the drawings, FIG. 1 shows a schematic view of a system 10 of the invention in the bistatic configuration, and FIG. 2 shows a schematic view of a system 20 of the invention in the monostatic configuration, for BRDF measurements.

In accordance with a preferred feature of the invention, systems 10 and 20 include an FTS 11,21 as a source for generating broadband radiation from the UV to the far IR. It is noted that other broadband sources may be used as would occur to the skilled artisan practicing the invention guided by these teachings, and the selection of an FTS is not considered limiting of the invention. Commercially available spectrometers may be used in system 10 and 20 of the invention, such as a Bio-Rad FTS-6000 (Bio-Rad Laboratories, Inc., Digilab Division, 237 Putnam Avenue, Cambridge Mass. 02139), a Bomem DA8 (ABB Bomem, 450 St. Jean Baptiste Avenue, Quebec Canada), or a Nicolet Nexus 870 (Nicolet Instrument Corporation, 5225 Verona Road, Madison Wis. 53711). The selected spectrometer is preferably computer-controlled with a software system allowing additional software to be written in a standard language or within a standard system environment to allow control override on the instrument, and to allow any additional hardware and data processing required for collection and reduction of data. This invention includes software to perform data acquisition, control of polarization elements, and polarimetric processing.

Spectropolarimetric measurements utilizing the invention in either of the system 10,20 embodiments are obtained by including in the systems a dual rotating retarder Mueller matrix polarimeter arrangement. In system 10, the polarimeter includes a polarization state generator (PSG) 12 comprising a linear polarizer 12a followed by a quarter wave retarder 12b and a polarization state analyzer (PSA) 13 comprising a quarter wave retarder 13a followed by a linear polarizer 13b. Rotational control of PSG 12 elements 12a, 12b individually may be accomplished using any convenient means such as computer controlled rotary stage system 12c.

Likewise, controlled rotation of PSA 13 elements 13a,13b may be accomplished individually using means such as computer controlled rotary stage system 13c. Sample 14 is in optical alignment between PSG 12 and PSA 13, substantially as shown in FIG. 1, so that beam 15 of radiation generated by FTS 11 may be directed along an optical axis extending through PSG 12, reflected off sample 14 passed through PSA 13 and onto detector 16. In system 20, the polarimeter includes PSG 22, including linear polarizer 22a, quarter wave retarder 22b and rotary stage system 22c structured similarly to PSG 12, and PSA 23, including quarter wave retarder 23a, linear polarizer 23b and rotary stage system 23c, structured like PSA 13. Sample 24 and beamsplitter 27 were disposed in optical alignment between PSG 22 and PSA 23 so that beam 25 of radiation generated by FTS 21 was directed along an optical axis extending through PSG 22 and beamsplitter 27, reflected off sample 14, passed through beamsplitter 27 again and PSA 13 and onto detector 26. The structure and functions of PSG 12,22 and PSA 13,23 are substantially the same as that described for corresponding elements in the system described in Goldstein et al '701 which description is incorporated here by reference. Data reduction and analysis for the Mueller matrix polarimeter of the systems of the invention are set forth in Goldstein et al '701 as described by Azzam ("Photopolarimetric Measurement of the Mueller Matrix by Fourier Analysis of a Single Detected Signal," *Opt Lett*, 2(6), 148–150 (1978)). Error correction used to compensate for imperfect or misaligned polarization elements in the data reduction is described in Goldstein et al ("Error Analysis of Mueller Matrix Polarimeters," *J Opt Soc Am*, 7(4), 693–700 (1990)) and Chenault et al ("Mueller Matrix Algorithms," *Proc. SPIE* 1746, 231–246 (July 1992)).

Use of an FTS as the spectral source within systems 10,20 allows the spanning of a whole spectrum in a very short time, with all the light from a single broad band source going through the sample, or reflecting off the sample, at once. The range of these spectrometers is generally from about 0.158 μm in the UV to hundreds of μm in the far IR. The source, beamsplitter and detector have to be changed to cover this whole range. Standard or custom sources may be selected for use within the spectrometer, as would occur to the skilled artisan practicing the invention, including deuterium sources for the UV, xenon sources for the UV-visible-near IR region, halogen sources for the near IR, globar sources for the IR and mercury arc lamps for the far IR (beyond 25 μm).

In systems described herein as built in demonstration of the invention, a Bio-Rad FTS-6000 spectrometer with a Win-IR Pro software system (Bio-Rad Laboratories Inc., Digilab Division, 237 Putnam Avenue, Cambridge Mass. 02139) was used. The spectrometer was configured for operation from about 0.2 to about 25 μm, similarly to that described in Goldstein et al '701 for measurements in transmission. The desired spectral range was spanned using a xenon source, halogen lamp and a globar as sources. Some spectral overlap among the sources can be expected. Three beamsplitters were used in system 20 for this range, a UV quartz, a near IR quartz and an IR KBr. Four detectors were used, including a photomultiplier, silicon, InSb and HgCdTe detectors. Other equivalent sources, beamsplitter materials and detector kinds may be selected as would occur to the skilled artisan practicing the invention, the specific selection (s) not considered limiting of the invention.

Referring now specifically to FIG. 1, in system 10 for bistatic measurements, detector 16 is disposed on platform 17 rotatable about a central vertical axis using a computer-controlled motor 18 operatively attached to platform 17. Sample 14 is mounted central of platform 17 and substantially vertically (with respect to the plane of FIG. 1) on a computer-controlled motorized rotational stage 19 that may be rotated to any angular position relative to the direction of beam 15 and rotatable platform 17. In the demonstration system 10, detector 16 assembly included an off-axis parabolic mirror of one inch focal length and one inch diameter that focuses a semi-collimated beam from FTS 11 onto detector 16. The mirror was fixed to look toward the central axis of the detector platter 17 and focus light onto the detector mounted perpendicularly to the light coming from the central axis. Detector 16 was rotatable to any position around sample 14, except to within a few degrees of the beam 15 direction where light from FTS 11 may be blocked. Spectropolarimetric data is collected after platform 17 and stage 19 are rotated to place sample 14 and detector 16 in the desired geometric relationship.

Referring specifically to FIG. 2, shown therein is a schematic of system 20 for monostatic measurements according to the invention. The elements, FTS 21, PSG 22, PSA 23, and detector 26 have function and structure corresponding to respective similarly named elements of FIG. 1. As indicated above, beamsplitter 27 is included in the optical path of beam 25 from FTS 21. Sample 24 is mounted on rotatable stage 19' central of rotatable platform 17' each operatively connected to and controlled by computer controlled motor 18' substantially the same as corresponding elements of FIG. 1. Operation of stage 19' and platform 17' in obtaining spectropolarimetric measurements on sample 24 is substantially the same as system 10 except that detector 26 does not reside on platform 17' as in FIG. 1. In taking measurements using system 20, source beam 25 passes through beamsplitter 27 before reaching sample 24. Beamsplitter 27 is positioned to direct the return beam toward detector 26 that remains fixed throughout the measurements. Sample 24 is rotated to the desired angle using stage 19' and platform 17 prior to the collection of data. Complete polarimetric information may require that beamsplitter 27 be rotated 90° about the optical path and detector 26 and PSA 23 be likewise rotated 90° around the optical path and out of the plane of the drawing.

Because spectral measurements are made with this instrument, polarizers and retarders should be as achromatic as possible. Polarizers are generally achromatic over their region of useful transmission. Retarders are not generally achromatic, although some retarders that are achromatic over specific spectral regions are available commercially. In the present instrument, some commercial retarders are used and some specially designed retarders, particularly for the IR, are used (see Goldstein et al, "Infrared Spectropolarimetry," *Opt Eng*, 28(2), 120–125 (1989); and Chipman et al, U.S. Pat. No. 4,961,634, "Infrared Achromatic Retarder," (October 1990)).

In order to obtain spectropolarimetric measurements using the invention, the optical and polarization elements must first be aligned. For example, in the FIG. 1 system, detector 16 is rotated on detector platform 17 to a point opposite the PSG 12 position. Optical beam 15 is then aligned to detector 16 without the polarization elements in place. The polarization elements (of PSG 12 and PSA 13) are then placed into beam 15 in order and aligned such that the polarization axes of the polarizers and the fast axes of the retarders are all aligned. A calibration run is then performed with detector 16 rotated into a position opposite PSG 12, and Mueller matrix data collection is performed without sample 14 in place. The calibration run establishes the remaining errors in orientation and retardation of the retarders, which errors are compensated for during sample data reduction.

Normal data collection comprises the calibration run and one or more sample runs, each of which is initiated by setting a number of spectrometer parameters and the geometrical relationships of the sample and detector. Once these are set, the instrument automatically collects and processes the data. The output includes the Mueller matrix of the sample as well as derived quantities such as retardance and diattenuation. Polarization BRDF measurements as a function of angle between source and detector can be constructed from the results.

The use of the FTS as the source provides rapid but complete spectral information over broad spectral regions, and the use of the dual rotating retarder configuration for the polarimeter provides complete information about the polarization properties of the sample, a combination of advantages that no other instrument can provide. The invention can be configured to measure samples, such as liquids or soils, that remain substantially horizontal during measurements by appropriate orientation of the FTS beam, the PSG and PSA elements, and the detector relative to the sample, all as would occur to the skilled artisan guided by these teachings.

The entire teachings of all references cited herein are hereby incorporated by reference.

The invention therefore provides a spectropolarimetric reflectometer for measuring the polarization characteristics of materials in reflection over broad wavelength regions. It is understood that modifications to the invention may be made as might occur to one skilled in the field of the invention within the scope of the appended claims. All embodiments contemplated hereunder that achieve the objects of the invention have therefore not been shown in complete detail. Other embodiments may be developed without departing from the spirit of the invention or from the scope of the appended claims.

We claim:

1. A bistatic spectropolarimetric reflectometer system for measuring polarimetric reflection properties of a material over broad spectral wavelength regions, comprising:

(a) a radiation source for generating radiation over a predetermined broad spectral range from the ultraviolet to the infrared and directing a beam of said radiation along an optical axis;

(b) an optical detector;

(c) a rotatable platform for supporting a sample of material substantially centrally thereon, and means operatively connected to said platform for selectively rotating said platform;

(d) first set of polarization elements defining a polarization state generator and including a rotatable linear polarizer followed by a rotatable quarter wave retarder, said polarization state generator disposed along said optical axis for directing said beam onto the sample;

(e) a second set of polarization elements defining a polarization state analyzer and including a rotatable quarter wave retarder followed by a rotatable linear polarizer, said polarization state analyzer disposed along said optical axis for directing the entire spectral range of said beam reflected from the sample onto said detector; and (f) wherein said detector includes means for processing said beam and providing data output including the Mueller matrix of the sample.

2. The system of claim 1 wherein said detector and said polarization state analyzer are disposed on said platform in optical alignment with said beam reflected from the sample.

3. The system of claim 1 further comprising a computer controlled motor operatively connected to said platform for selectively rotating said platform.

4. The system of claim 1 wherein said radiation source is a Fourier transform spectrometer.

5. The system of claim 4 wherein said spectrometer is computer-controlled with a software system for collection and reduction of data, control of polarization elements, and polarimetric processing.

6. The system of claim 4 wherein the spectral range of said spectrometer is in the range of from about 0.2 micron in the ultraviolet to about 25 microns in the infrared.

7. The system of claim 4 wherein said spectrometer includes a deuterium source for the ultraviolet spectral range, a xenon source for the ultraviolet to near infrared spectral range, a halogen source for the near infrared spectral range, a globar source for the infrared spectral range, and a mercury arc lamp for the far infrared spectral range.

8. The system of claim 1 wherein said detector is selected from the group consisting of photomultiplier, silicon, InSb and HgCdTe detectors.

9. A monostatic spectropolarimetric reflectometer system for measuring polarimetric reflection properties of a material over broad spectral wavelength regions, comprising:

(a) a radiation source for generating radiation over a predetermined broad spectral range from the ultraviolet to the infrared and directing a beam of said radiation along an optical axis;

(b) an optical detector;

(c) a rotatable platform for supporting a sample of material substantially centrally thereon, and means operatively connected to said platform for selectively rotating said platform;

(d) first set of polarization elements defining a polarization state generator and including a rotatable linear polarizer followed by a rotatable quarter wave retarder, said polarization state generator disposed along said optical axis between said source and the sample;

(e) a second set of polarization elements defining a polarization state analyzer and including a rotatable quarter wave retarder followed by a rotatable linear polarizer, said polarization state analyzer disposed along said optical axis between the sample and said detector;

(f) a beamsplitter disposed along said optical axis between said polarization state generator and the sample for directing the entire spectral range of said beam from said polarization state generator onto the sample and for directing the entire spectral range of said beam projected by said polarization state analyzer onto said detector; and (g) wherein said detector includes means for processing said beam and providing data output including the Mueller matrix of the sample.

10. The system of claim 9 further comprising a computer controlled motor operatively connected to said platform for selectively rotating said platform.

11. The system of claim 9 wherein said radiation source is a Fourier transform spectrometer.

12. The system of claim 11 wherein said spectrometer is computer-controlled with a software system for collection and reduction of data, control of polarization elements, and polarimetric processing.

13. The system of claim 11 wherein the spectral range of said spectrometer is in the range of from about 0.2 micron in the ultraviolet to about 25 microns in the infrared.

14. The system of claim 11 wherein said spectrometer includes a deuterium source for the ultraviolet spectral range, a xenon source for the ultraviolet to near infrared spectral range, a halogen source for the near infrared spectral range, a globar source for the infrared spectral range, and a mercury arc lamp for the far infrared spectral range.

15. The system of claim 9 wherein said detector is selected from the group consisting of photomultiplier, silicon, InSb and HgCdTe detectors.

* * * * *